United States Patent [19]

Boyer

[11] 4,414,396
[45] Nov. 8, 1983

[54] POLYHALOPHTHALIMIDOALKYL-FUNCTIONAL CARBONATES AND HALOFORMATES

[75] Inventor: Nicodemus E. Boyer, Schaumburg, Ill.

[73] Assignee: PPG Industries, Inc., Pittsburgh, Pa.

[21] Appl. No.: 337,660

[22] Filed: Jan. 7, 1982

[51] Int. Cl.$^3$ .......................................... C07D 209/48
[52] U.S. Cl. ....................................... 548/478; 524/99; 524/565; 524/566; 524/577; 524/578; 524/585; 524/586; 548/462; 562/451
[58] Field of Search .......................................... 548/478

[56] References Cited

U.S. PATENT DOCUMENTS

| | | | |
|---|---|---|---|
| 2,451,637 | 10/1948 | Strain et al. | 260/326 |
| 2,657,169 | 10/1953 | Ligett et al. | 167/33 |
| 2,863,801 | 12/1958 | Kuhle et al. | 167/33 |
| 3,240,792 | 3/1966 | Patrick et al. | 260/346.3 |
| 3,251,855 | 5/1966 | Schumann | 260/326 |
| 3,313,763 | 4/1967 | Creighton et al. | 260/41 |
| 3,354,177 | 11/1967 | Seeliger | 260/326 |
| 3,624,024 | 11/1971 | Caldwell et al. | 260/40 R |
| 3,663,495 | 5/1972 | Michael et al. | 260/37 N |
| 3,868,388 | 2/1975 | Dotson et al. | 260/326 N |
| 3,873,567 | 3/1975 | Cyba | 260/326 C |
| 3,915,930 | 10/1975 | Dotson et al. | 260/45.8 N |
| 3,978,079 | 8/1976 | Bollyky et al. | 260/326 N |
| 4,003,862 | 1/1977 | Albright | 260/2.5 AJ |
| 4,125,535 | 11/1978 | Wolford | 260/326 N |
| 4,140,862 | 2/1979 | Dotson et al. | 560/83 |
| 4,197,133 | 4/1980 | Zweifel et al. | 430/195 |
| 4,250,096 | 2/1981 | Kvita et al. | 260/326 N |
| 4,263,222 | 4/1981 | Ching | 260/463 |

FOREIGN PATENT DOCUMENTS

| | | |
|---|---|---|
| 47-5539 | 2/1972 | Japan . |
| 47-27138 | 7/1972 | Japan . |
| 47-44981 | 11/1972 | Japan . |
| 1287934 | 9/1972 | United Kingdom . |

OTHER PUBLICATIONS

E. Bosies et al., Chem. Abstracts 90:203849q (1979).
Pratt et al., "Phthalic Acid Derivatives . . . ", Journal of the American Chemical Society, vol. 40, pp. 1415–1425 (1918).
Spatz et al., "Use of Tetrabromophthalic Anhydrice . . . ", I&EC Product Research and Development, vol. 8, No. 4, pp. 381–391 (1969).
Spatz et al. "Discoloration of Tetrabromophthalic Anhydride Polyester Resins", I&EC Product Research and Development, vol. 8, No. 4, pp. 391–396 (1969).
Spatz et al., "Some N–Substituted Tetrabromophthalimide Fire-Retardant Additives" I&EC Product Research and Development, vol. 8, No. 4, pp. 397–398 (1969).
Chemical Abstracts, vol. 77, 5211u (1972).
Chemical Abstracts, vol. 78, 73530t (1973).
Chemical Abstracts, vol. 80, 84584f (1974).

Primary Examiner—Donald G. Daus
Assistant Examiner—M. C. Eakin
Attorney, Agent, or Firm—George D. Morris

[57] ABSTRACT

Polyhalophthalimidoalkyl-functional carbonates may be employed as fire retardant additives to polymers. Examples of such carbonates are 2-(tetrabromophthalimido)ethyl 2,4,6-tribromophenyl carbonate, 2-(tetrabromophthalimido)ethyl pentabromophenyl carbonate and bis[2-(tetrabromophthalimido)ethyl] carbonate.

Polyhalophthalimidoalkyl haloformates, N-(hydroxyalkyl)-polyhalophthalimides, and 2-(hydroxyalkylcarbamyl)-polyhalobenzoic acids are useful as intermediates in the preparation of the carbonates.

5 Claims, No Drawings

POLYHALOPHTHALIMIDOALKYL-FUNCTIONAL CARBONATES AND HALOFORMATES

The present invention provides compounds which are fire retardant and which are especially useful when in admixture with one or more polymers. Accordingly, the present invention provides compounds represented by the structural formula:

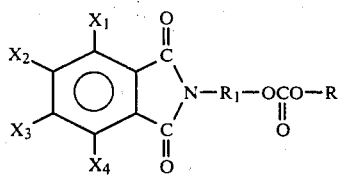

wherein
a. R is

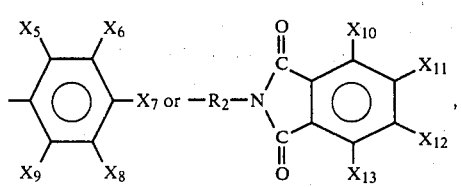

b. $R_1$ and $R_2$ are each independently straight chain or branched alkylene having from about 2 to about 5 carbon atoms, and
c. $X_1$, $X_2$, $X_3$, $X_4$, $X_5$, $X_6$, $X_7$, $X_8$, $X_9$, $X_{10}$, $X_{11}$, $X_{12}$, and $X_{13}$ are each independently hydrogen, chloro or bromo, with the provisos that:
 (1) at least three of $X_1$, $X_2$, $X_3$, and $X_4$ are each independently chloro or bromo,
 (2) at least three of $X_5$, $X_6$, $X_7$, $X_8$, and $X_9$ are each independently chloro or bromo, and
 (3) at least three of $X_{10}$, $X_{11}$, $X_{12}$, and $X_{13}$ are each independently chloro or bromo.

Typically, $R_1$ and $R_2$ are each independently straight chain or branched alkylene having from about 2 to about 4 carbon atoms. Straight chain alkylene is preferred. It is especially preferred that $R_1$, $R_2$, or both $R_1$ and $R_2$ be ethylene.

The halo groups of each of the two aromatic rings of the carbonate compound may be mixed; the halo groups of only one ring may be identical while those of the other are mixed; the halo groups of one ring may be the same but different from the halo groups of the other ring which are themselves the same; or the halo groups of both rings may be the same. It is preferred that $X_1$, $X_2$, $X_3$, $X_4$, $X_{10}$, $X_{11}$, $X_{12}$, and $X_{13}$ each be bromo and that $X_5$, $X_6$, $X_7$, $X_8$, and $X_9$ each independently be hydrogen or bromo with the proviso that at least three of $X_5$, $X_6$, $X_7$, $X_8$ and $X_9$ are bromo.

For R, the preferred groups are 2,4,6-tribromophenyl, pentabromophenyl and 2-(tetrabromophthalimido)ethyl.

Compounds which exemplify the carbonates of the invention are:

2-(tetrabromophthalimido)ethyl 2,4,6-tribromophenyl carbonate
2-(tetrabromophthalimido)ethyl 2,3,4,6-tetrabromophenyl carbonate
3-(tetrabromophthalimido)propyl 2,4,6-tribromophenyl carbonate
5-(tetrabromophthalimido)pentyl 2,4,6-tribromophenyl carbonate
2-(tetrabromophthalimido)-1-methylethyl 2,4,6-tribromophenyl carbonate
2-(tetrachlorophthalimido)ethyl 2,4,6-tribromophenyl carbonate
2-(tetrabromophthalimido)ethyl 2,4,6-trichlorophenyl carbonate
2-(tetrachlorophthalimido)ethyl 2,4,6-trichlorophenyl carbonate
2-(tetrabromophthalimido)ethyl pentabromophenyl carbonate
3-(tetrabromophthalimido)propyl pentabromophenyl carbonate
5-(tetrabromophthalimido)pentyl pentabromophenyl carbonate
2-(tetrabromophthalimido)ethyl 2,4,6-tribromo-3,5-dichlorophenyl carbonate
2-(tetrabromophthalimido)-1-ethylethyl pentabromophenyl carbonate
2-(tetrachlorophthalimido)ethyl pentabromophenyl carbonate
2-(tetrabromophthalimido)ethyl pentachlorophenyl carbonate
2-(tetrachlorophthalimido)ethyl pentachlorophenyl carbonate
5-(tetrachlorophthalimido)pentyl 2,4-dibromo-3,5,6-trichlorophenyl carbonate
bis[2-(tetrabromophthalimido)ethyl] carbonate
bis[2-(tetrachlorophthalimido)ethyl] carbonate
bis[5-(tetrachlorophthalimido)pentyl] carbonate
2-(tetrabromophthalimido)ethyl 2-(tetrachlorophthalimido)ethyl carbonate
2-(tetrabromophthalimido)ethyl 2-(3,4,6-tribromophthalimido)ethyl carbonate
2-(tetrabromophthalimido)ethyl 2-(3,4,5-tribromophthalimido)ethyl carbonate
2-(tetrabromophthalimido)ethyl 2-(3,4,6-trichlorophthalimido)propyl carbonate
bis[2-(3,4,6-tribromophthalimido)ethyl] carbonate
bis[2-(3,4,5-tribromophthalimido)ethyl] carbonate
bis[2-(3,4,6-trichlorophthalimido)ethyl] carbonate
bis[3-(3,4,5-trichlorophthalimido)propyl] carbonate
2-(3,4,6-tribromophthalimido)ethyl 2,4,6-tribromophenyl carbonate
2-(3,4,6-tribromophthalimido)-1-methylethyl pentabromophenyl carbonate
2-(3,4,6-tribromophthalimido)ethyl 2,4,6-tribromo-3,5-dichlorophenyl carbonate
2-(3,4,5-trichlorophthalimido)ethyl pentabromophenyl carbonate Minor additional substituents may be attached to the molecule so long as their identities and their numbers do not seriously interfere with the fire retardant properties of the compound.

As used in the present specification and claims, locants in the phthalimido group are identified as follows:

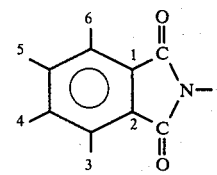

Accordingly, 3,4,6-tribromophthalimido is equivalent to 1,3-dihydro-1,3-dioxo-4,5,7-tribromo-2H-isoindol-2-yl.

The carbonates of the invention may be prepared by reacting haloformate represented by the structural formula:

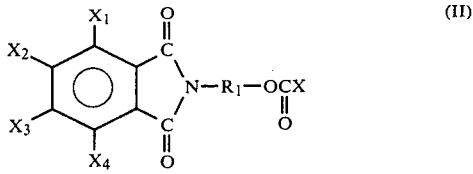

with halogen substituted phenol represented by the structural formula:

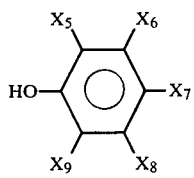

or N-(hydroxyalkyl)-polyhalophthalimide represented by the structural formula:

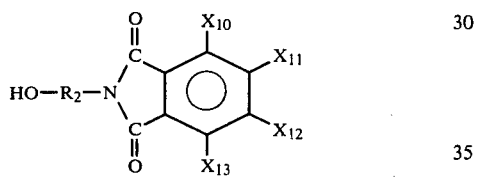

wherein X is chloro or bromo and wherein $R_1$, $R_2$, $X_1$, $X_2$, $X_3$, $X_4$, $X_5$, $X_6$, $X_7$, $X_8$, $X_9$, $X_{10}$, $X_{11}$, $X_{12}$, and $X_{13}$ are as discussed above with respect to Formula I.

Although X may be chloro or bromo, chloro is preferred.

The reaction may conveniently be conducted in an inert organic solvent. Ordinarily, one or more scavengers of hydrogen halide are also present. Some scavengers may also act as catalysts for the reaction and may be regenerated on heating by evolution of hydrogen halide.

The two reactants are usually employed in about stoichiometric amounts although an excess of either is acceptable. The ordinary practice is to use stoichiometric amounts or a slight excess of the hydroxy-functional reactant. Typically the molar ratio of the hydroxy-functional compound to the haloformate is in the range of from about 0.1:1 to about 10:1. From about 0.9:1 to about 1.1:1 is preferred.

Exemplary scavengers which may be used are nitrogen-containing heterocyclic organic compounds such as pyridine, imidazole, 2,6-lutidine, 2,4,6-collidine, and di(methylamino)pyridine. Non-heterocyclic nitrogen-containing aromatic scavengers such as dimethylaniline are also useful. Nitrogen-containing aliphatic compounds such as triethylamine may be employed as scavengers, as may inorganic bases such as sodium hydroxide, potassium hydroxide, sodium carbonate and potassium carbonate. Mixtures of scavengers may be used where desired. The preferred scavenger is pyridine.

The amount of scavenger employed is subject to wide variation. Normally the molar ratio of the scavenger to haloformate is in the range of from about 0.0001:1 to about 100:1. Typically it is in the range of from about 0.0005:1 to about 20:1. It is preferred that the molar ratio be in the range of from about 0.001:1 to about 1:1.

Substantially any solvent or mixture of solvents may be used so long as they are inert to the reactants and the reaction products at the reaction temperature and below. Examples of suitable solvents are the aromatic hydrocarbon solvents such as benzene, toluene, and xylene. Chlorinated aliphatic solvents such as methylene chloride, chloroform, perchloroethylene, trichloroethylene and carbon tetrachloride may be used. Similarly chlorinated aromatic solvents such as chlorobenzene, o-dichlorobenzene and o-chlorotoluene are useful. The preferred inert solvents are chlorobenzene and o-dichlorobenzene, while chlorobenzene is especially preferred.

The weight ratio of inert solvent to the reactants ultimately employed is subject to wide variation. Generally, the amount of solvent should be sufficient to at least partially dissolve the reactants at the reaction temperature. The weight ratio of inert solvent to the reactants ultimately employed is usually in the range of from about 0.5:1 to about 100:1. From about 2:1 to about 20:1 is preferred.

The temperature at which the reaction is conducted may also be widely varied. Reaction temperatures in the range of from about $-20°$ C. to about $+200°$ C. are most often employed. It is preferred that the reaction temperature be in the range of from about $50°$ C. to about $150°$ C.

According to one aspect of the invention, compounds represented by the structural formula:

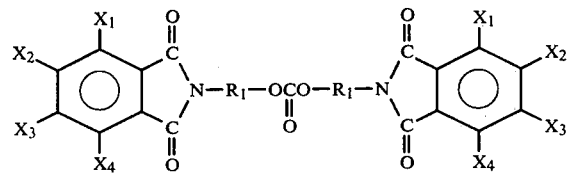

may be prepared by reacting N-(hydroxyalkyl)-polyhalophthalimide represented by the structural formula:

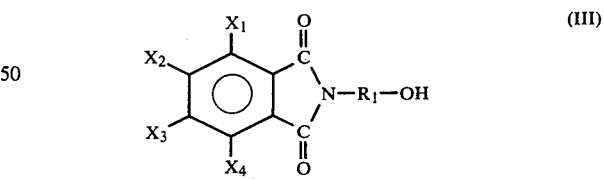

with carbonic dihalide, wherein $R_1$, $X_1$, $X_2$, $X_3$, and $X_4$ are as discussed above with respect to Formula I.

Examples of carbonic dihalides which may be used include phosgene, bromophosgene and bromochlorophosgene. The preferred carbonic dihalide is phosgene. Mixtures of carbonic dihalides may be used when desired.

This reaction may also be conducted in an inert organic solvent and preferably in the presence of a scavenger for hydrogen halide. The solvents and scavengers described above are satisfactory. The molar ratio of scavenger to carbonic dihalide may be widely varied, but it ordinarily is in the range of from about 0.0001:1 to about 100:1. From about 0.001:1 to about 2:1 is preferred. The amount of solvent may also be widely varied and is generally used in the proportions heretofore described.

The reaction temperature is similarly subject to wide variation. Temperatures in the range of from about $-20°$ C. to about $+150°$ C. are most often used. From about $0°$ C. to about $110°$ C. is preferred.

The reactants are generally used in about their stoichiometric amounts, but an excess of either may be introduced. The molar ratio of the hydroxy-functional compound to carbonic dihalide is usually in the range of from about 0.2:1 to about 20:1. From about 1.6:1 to about 2.2:1 is preferred.

According to yet another aspect of the invention, compounds represented by the structural formula:

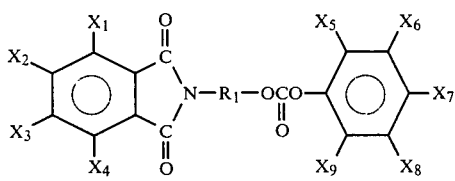

may be prepared by reacting N-(hydroxyalkyl)-polyhalophthalimide represented by Formula III with haloformate represented by the structural formula:

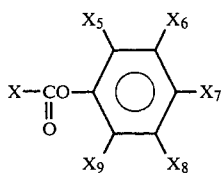

wherein X is chloro or bromo and wherein $R_1$, $X_1$, $X_2$, $X_3$, $X_4$, $X_5$, $X_6$, $X_7$, $X_8$, and $X_9$ are as discussed above with respect to Formula I.

The reaction may conveniently be conducted in an inert organic solvent and preferably in the presence of a scavenger for hydrogen chloride. The solvents and scavengers heretofore described are satisfactory. The molar ratio of scavenger to haloformate is subject to wide variation but it is usually in the range of from about 0.0001:1 to about 100:1. Typically it is in the range of from about 0.0005:1 to about 20:1. From about 0.001:1 to about 1:1 is preferred. The amount of solvent is also subject to wide variation and is generally employed in the proportions earlier described.

The reaction temperature may also be widely varied. Temperatures in the range of from about $-20°$ C. to about $+200°$ C. are most often used. From about $50°$ C. to about $150°$ C. is preferred.

The reactants are generally used in about their stoichiometric amounts but an excess of either may be introduced. The molar ratio of the hydroxy-functional compound to haloformate is usually in the range of from about 0.1:1 to about 10:1. From about 0.9:1 to about 1.1:1 is preferred.

Another aspect of the present invention provides a method for producing polyhalophthalimidoalkyl haloformate. This is accomplished by reacting N-(hydroxyalkyl)-polyhalophthalimide with carbonic dihalide. Examples of carbonic dihalides which may be used include phosgene, bromophosgene and bromochlorophosgene.

The reaction is generally conducted in an inert organic solvent and preferably in the presence of a scavenger for hydrogen halide. The solvents and scavengers discussed above are satisfactory. The molar ratio of scavenger to carbonic dihalide may be widely varied, but it ordinarily is in the range of from about 0.0001:1 to about 100:1. From about 0.0005:1 to about 20:1 is typical. From about 0.001:1 to about 1:1 is preferred. The amount of solvent may also be widely varied and is generally used in the proportions earlier described.

The reactants are generally employed in about their stoichiometric amounts, although an excess of either may be introduced. The molar ratio of the hydroxy-functional compound to carbonic dihalide may be widely varied, but it is typically in the range of from about 0.1:1 to about 10:1. From about 0.9:1 to about 2:1 is preferred.

The reaction temperature may be widely varied. Temperatures in the range of from about $-20°$ C. to about $+200°$ C. are most often used. From about $50°$ C. to about $150°$ C. is preferred.

Ordinarily the hydroxyalkyl group of the N-(hydroxyalkyl)-polyhalophthalimide contains from about 2 to about 5 carbon atoms. From about 2 to about 4 carbon atoms is typical. The alkyl portion may be straight chain or branched, but the former is preferred. The preferred hydroxyalkyl group is 2-hydroxyethyl.

Each halo group of the N-(hydroxyalkyl)-polyhalophthalimide may be independently chloro or bromo. Usually all the halo groups are either chloro or bromo. Preferably all are bromo.

Polyhalophthalimidoalkyl haloformates represented by Formula II, wherein X, $R_1$, $X_1$, $X_2$, $X_3$ and $X_4$ are as discussed above, may conveniently be prepared by this method. They may be used as intermediates in the preparation of the fire retardant carbonates of the invention as well as for the preparation of other compounds.

N-(Hydroxyalkyl)-polyhalophthalimide may conveniently be prepared by reacting aminoalkanol with polyhalophthalic anhydride.

The reaction is usually conducted in an inert organic solvent. The weight ratio of inert solvent to the reactants is subject to wide variation, but it ordinarily should be sufficient to at least partially dissolve the reactants at the reaction temperature. The weight ratio of inert solvent to the reactants ultimately employed is generally in the range of from about 0.5:1 to about 100:1. From about 2:1 to about 20:1 is preferred.

Examples of suitable solvents include aromatic hydrocarbon solvents, chlorinated aromatic solvents and chlorinated aliphatic solvents, examples of which are enumerated above. The preferred solvent is chlorobenzene.

The reaction temperature may be varied, but it is typically in the range of from about $50°$ C. to about $200°$ C. From about $80°$ C. to about $150°$ C. is preferred.

The preferred subclasses of polyhalophthalic anhydride are tetrahalophthalic anhydride and trihalophthalic anhydride.

Each halo group of the polyhalophthalic anhydride may be independently chloro or bromo, but most often they are either all chloro or all bromo. Examples of these compounds are 3,4,5-trichlorophthalic anhydride, 3,4,6-trichlorophthalic anhydride, tetrachlorophthalic anhydride, 3,4,5-tribromophthalic anhydride, 3,4,6-tribromophthalic anhydride, and tetrabromophthalic anhydride. The preferred compounds are tetrachlorophthalic anhydride and tetrabromophthalic anhydride, with the latter especially preferred.

The aminoalkanol employed generally contains from about 2 to about 5 carbon atoms. From about 2 to about 4 carbon atoms is typical. The α-amino-ω-alkanols are preferred. Examples of aminoalkanols which may be used include 2-aminoethanol, 3-amino-1-propanol, 4-amino-1-butanol, 5-amino-1-pentanol, 2-amino-1-propanol, 1-amino-2-propanol, 2-amino-1-butanol, 2-amino-2-methyl-1-propanol and 2-amino-3-methyl-1-butanol. The preferred aminoalkanol is 2-aminoethanol.

Although it is not desired to be bound by any theory, it is believed that the polyhalophthalic anhydride reacts with the aminoalkanol to form the corresponding 2-(hydroxyalkylcarbamyl)-polyhalobenzoic acid which then condenses to form the corresponding N-(hydroxyalkyl)-polyhalophthalimide.

When the polyhalophthalic anhydride is reacted with aminoalkanol at temperatures in the range of from about 110° C. to about 200° C., the product is essentially the N-(hydroxyalkyl)-polyhalophthalimide. When the reaction temperature is in the range of from about 60° C. to about 90° C., both the N-(hydroxyalkyl)-polyhalophthalimide and the 2-(hydroxyalkylcarbamyl)-polyhalobenzoic acid are formed in significant amounts. When the reaction temperature is in the range of from about 0° C. to about 50° C., the product is essentially 2-(hydroxyalkylcarbamyl)-polyhalobenzoic acid. It should be recognized that there are probably no sharp lines of demarkation between temperatures which produce one product or the other. Rather, it appears that as the reaction temperature is increased, the proportion of the substituted phthalimide produced at the expense of the substituted benzoic acid, increases. According to a further embodiment of the invention, therefore, 2-(hydroxyalkylcarbamyl)-polyhalobenzoic acid is prepared by reacting aminoalkanol with polyhalophthalic anhydride wherein 2-(hydroxyalkylcarbamyl)-polyhalobenzoic acid collects in the reaction mixture.

The reaction is generally conducted in an inert organic solvent. The weight ratio of the inert solvent to the reactants is subject to wide variation, but it usually should be sufficient to at least partially dissolve the reactants at the reaction temperature. The weight ratio of inert solvent to the reactants ultimately employed is generally in the range of from about 0.5:1 to about 100:1. From about 2:1 to about 20:1 is preferred.

Examples of suitable solvents include aromatic hydrocarbon solvents, chlorinated aromatic solvents and chlorinated aliphatic solvents, examples of which are given above. The preferred solvent is chlorobenzene.

The reaction temperature may be varied, but it is ordinarily in the range of from about 0° C. to about 90° C. From about 0° C. to about 50° C. is preferred.

The previous discussions respecting the preferred subclasses of polyhalophthalic anhydride, the halo groups of the polyhalophthalic anhydride, the preferred polyhalophthalic anhydrides, the types of aminoalkanol generally employed and the preferred aminoalkanol being 2-aminoethanol are also applicable to this method. The 2-(hydroxyalkylcarbamyl)-polyhalobenzoic acid may be separated from the other components of the reaction mixture or not so separated as desired, and heated to form N-(hydroxyalkyl)-polyhalophthalimide. It may also be used, generally but not necessarily after separation from the other components of the reaction mixture, as a reactant in the formation of compounds other than N-(hydroxyalkyl)-polyhalophthalimide.

The method may be used to prepare compounds represented by the structural formula

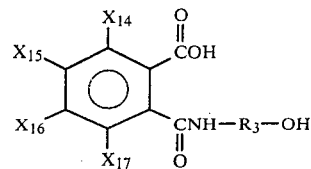

wherein:
a. $R_3$ is straight chain or branched alkylene having from about 2 to about 5 carbon atoms, and
b. $X_{14}$, $X_{15}$, $X_{16}$, and $X_{17}$ are each independently hydrogen, chloro or bromo, with the proviso that at least three of $X_{14}$, $X_{15}$, $X_{16}$, and $X_{17}$ are each independently chloro or bromo.

Typically $R_3$ is straight chain or branched alkylene having from about 2 to about 4 carbon atoms. Straight chain alkylene is preferred. It is especially preferred that $R_3$ be ethylene.

The halo groups of the aromatic ring may be mixed or they may be the same. It is preferred that they be the same. It is especially preferred that $X_{14}$, $X_{15}$, $X_{16}$, and $X_{17}$ each be either chloro or bromo.

Compounds which exemplify the 2-(hydroxyalkylcarbamyl)-polyhalobenzoic acids include
2-[(2-hydroxyethyl)carbamyl]-tetrabromobenzoic acid
2-[(2-hydroxyethyl)carbamyl]-tetrachlorobenzoic acid
2-[(2-hydroxyethyl)carbamyl]-3,4,5-tribromobenzoic acid
2-[(2-hydroxyethyl)carbamyl]-3,4,6-tribromobenzoic acid
2-[2-hydroxyethyl)carbamyl]-4,5,6-tribromobenzoic acid
2-[(2-hydroxyethyl)carbamyl]-3,5,6-tribromobenzoic acid
2-[(2-hydroxyethyl)carbamyl]-3,4,5-trichlorobenzoic acid
2-[(2-hydroxyethyl)carbamyl]-3,4,6-trichlorobenzoic acid
2-[(2-hydroxyethyl)carbamyl]-3,5,6-trichloro-4-bromobenzoic acid
2-[(3-hydroxypropyl)carbamyl]-tetrabromobenzoic acid
2-[(2-hydroxy-2-methylethyl)carbamyl]-3,5,6-trichlorobenzoic acid
2-[(4-hydroxybutyl)carbamyl]-tetrachlorobenzoic acid
2-[(3-hydroxy-2-methylpropyl)carbamyl]-4,5,6-tribromobenzoic acid
2-[5-(hydroxypentyl)carbamyl]-tetrabromobenzoic acid Each of the various reactions described above is ordinarily conducted at or near ambient atmospheric pressure, although greater or lesser pressures may be used where desired.

The polyhalophthalimidoalkyl-functional carbonate of the invention may be incorporated with flammable polymer to provide a composition having greater fire retardancy than that of the flammable polymer. The individual carbonates of the invention will be more effective with some flammable polymers than with others, but the desired effect can be obtained by proper adjustment of the fire retardant carbonate concentration in the composition. Usually the flammable polymer is thermoplastic, but it may be thermosetting. The flammable polymer may be a homopolymer, an interpolymer or a mixture of polymers. Examples of flammable polymers in which the fire retardant polymer of the invention may be used include acrylonitrile-butadiene-styrene interpolymer or graft polymer, polystyrene, high density polyethylene, low density polyethylene, polypropylene, polyesters, and polycarbonates. The preferred polymers are acrylonitrile-butadiene-styrene interpolymer or graft polymer, high impact polystyrene and high density polyethylene.

The amount of the fire retardant carbonate which is present in compositions of the invention is subject to wide variation. Such fire retardant carbonate is ordinarily present in an amount in the range of from about 2 percent to about 30 percent by weight of the polymer. From about 5 percent to about 20 percent by weight is preferred. Mixtures of fire retardant carbonates may be used.

Other materials which increase fire retardancy may optionally also be present in the composition. Examples of such materials include zinc oxide, zinc borate, boric acid, borax, ferric oxide, antimony trioxide and antimony pentoxide. Antimony trioxide is preferred. Mixtures may be employed where desired. The amounts of these materials are also subject to wide variation. When used, they are usually present in the composition of the invention in an amount in the range of from about 0.1 to about 15 percent by weight. An amount in the range of from about 1 percent to about 10 percent by weight is preferred.

The compositions of the invention may optionally contain plasticizers, pigments, dyes, tints, resinous pigment dispersants or grinding vehicles, and the like.

The listing of optional ingredients discussed above is by no means exhaustive. These and other ingredients may be employed in their customary amounts for their customary purposes so long as they do not seriously interfere with good polymer formulating practice.

The compositions of the invention are usually prepared by simply admixing the various ingredients. This may be accomplished in many instances by milling. If the flammable polymer and the fire retardant polymer are both soluble in solvent, they may be dissolved, mixed, and the polymer mixture recovered by removal of the solvent. Most often, the materials are admixed while the polymer is in the form of a melt.

The compositions of the invention have fire retardant characteristics and find many uses. Typically, they may be extruded into fibers, films or other shapes, or molded, shaped or formed into substantially any form. Where the polymers of the composition are soluble in solvent or are dispersible in liquid nonsolvents such as water, organic nonsolvent or miscible systems of water and organic liquid, the composition may be employed in coating compositions.

In the illustrative examples which follow, all parts are parts by weight and all percentages are percentages by weight unless otherwise specified.

EXAMPLE I

This example illustrates a synthesis of N-(2-hydroxyethyl)tetrabromophthalimide and a synthesis of 2-[(2-hydroxyethyl)carbamyl]-tetrabromobenzoic acid.

A 4-liter beaker was charged with 927.4 grams (2 moles) of tetrabromophthalic anhydride and 2.7 liters of chlorobenzene. The charged materials were heated to 90° C., but not all of the tetrabromophthalic anhydride dissolved.

An additive solution was prepared by combining 122.2 grams (2 moles) of 2-aminoethanol and 350 milliliters of chlorobenzene and heating to 99° C.

Over a period of 1 hour the additive solution was added with stirring to the contents of the beaker. After 150 milliliters had been added, the temperature of the reaction mixture was 103° C. and about all of the tetrabromophthalic anhydride was dissolved. After completion of the addition, with the temperature of the reaction mixture at slightly above 120° C., the reaction mixture phase separated into a lower liquid layer of about 700 milliliters and an upper liquid layer. The reaction mixture was allowed to cool gradually almost to room temperature, whereupon the lower liquid layer solidified to a white solid. The solid was collected by filtration as first crop solids, pulverized to an off-white powder and dried in a vacuum oven at 120° C. and an absolute pressure of 0.5 Torr to produce 769.7 grams of oven dried first crop solids. The filtrate was cooled to 25° C. and refiltered to recover white crystals as second crop solids. The second crop was air-dried for 20 hours in an open dish to produce 171.2 grams of air-dried second crop solids. These were then dried in a vacuum oven at 160° C. and an absolute pressure of 0.5 Torr to produce 154.8 grams of oven-dried second crop solids. The filtrate from the second crop was concentrated almost to dryness by distillation of chlorobenzene in a flash evaporator. The residue was filtered and washed with 30 milliliters of methanol to obtain a third crop white solid. This was dried in a manner similar to that used to dry the second crop to produce 39.4 grams of oven-dried third crop solids. The various crops were analyzed by liquid chromatography. The results, which are shown in Table 1, are described as being relative because they are a function of the absolute weight percentages of the materials present as well as of specific ultraviolet absorptivities which are different for different compounds.

TABLE 1

| | | Analytical Results | | | |
| | Drying | Analysis, Relative Percent by Weight* | | | |
| Crop | Method | A | B | C | D |
|---|---|---|---|---|---|
| 1 | Oven | 96.2 | 0.2 | 0.2 | 2.9 |
| 2 | Air | 89.1 | 0.4 | 2.9 | 7.1 |
| 2 | Air and Oven | 94.6 | 0.3 | 2.0 | 2.0 |
| 3 | Air and Oven | 11.1 | 0.2 | 83.8 | 2.8 |

*A = N—(2-hydroxyethyl)-tetrabromophthalimide
B = chlorobenzene
C = tetrabromophthalic anhydride
D = 2-[2-(hydroxyethyl)carbamyl]-tetrabromobenzoic acid The data of Table 1 show that oven drying the air-dried second crop resulted in a considerable decrease in the amount of Compound D present and an approximately commensurate increase in the amount of Compound A. This indicates that Compound A may be prepared by heating Compound D in a vacuum oven at about 160° C. for several hours at reduced pressure.

EXAMPLE II

This example illustrates a synthesis of N-(2-hydroxyethyl)tetrabromophthalimide.

A first beaker was charged with 21.3 grams (0.349 mole) of 2-aminoethanol and 400 milliliters of glacial acetic acid to form a clear solution at 39° C.

A second beaker was charged with 141.9 grams (0.306 mole) of tetrabromophthalimide and 600 milliliters of glacial acetic acid. The materials were heated with stirring to 103° C. Two 400 milliliter portions of glacial acetic acid were added. Complete dissolution of solids was not observed at temperatures up to 85° C. Two 200 milliliter portions of acetone were added and the solids were allowed to settle out. The clear liquid layer was separated from the solids and while still hot (cooling from 88° C. to about 80° C.) was added with stirring to the clear solution of the first beaker to form a reaction mixture. No precipitate was observed at about 75° C. The reaction mixture was allowed to cool to room temperature. To the solids remaining in the second beaker were added two 200 milliliter portions of acetone. The resulting mixture was heated to 50° C., the solids were allowed to settle and the clear liquid was decanted from the solids and added to the reaction mixture. The solids remaining in the second beaker were heated to 160° C. and 180 milliliters of o-dichlorobenzene was added. The remaining solids were allowed to settle. The liquid was decanted from the solids, and while at a temperature of 150° C., was added to the reaction mixture. No precipitate was observed in the reaction mixture which was a clear, very pale yellow solution at 60° C. The solids remaining in the second beaker were dissolved in 180 milliliters of o-chlorotoluene and the solution was added while hot to the reaction mixture. No precipitate was observed at 60° C. The reaction mixture was heated to 80° C. in a four liter beaker and then removed from the hot plate. At this point the reaction mixture was a clear, pale greenish, nearly colorless solution with no solids present. The reaction mixture was allowed to stand open overnight in a hood during which time the volume was reduced by evaporation from about 2500 milliliters to about 2000 milliliters. The reaction mixture was then heated on the hot plate with stirring and boiling to reduce the volume from 2000 milliliters to 1500 milliliters. During the evaporation process, the reaction mixture was observed to become cloudy when the volume had been reduced to about 1800 milliliters.

The 1500 milliliters of reaction mixture was next divided into two portions and evaporated in a two liter flask using a flash evaporator to a total volume of about 1000 milliliters. A first crop of solids was removed by filtration, washed with 300 milliliters of acetone in several portions and dried at 128° C. to 130° C. at an absolute pressure of 5 Torr for two hours and fifty minutes. The resulting pale yellow solid had a melting range of 229° C. to 248° C. and weighed 121.4 grams.

The filtrate was gradually concentrated by flash evaporation and refiltered twice to produce second and third crops of white to off-white solids. The second crop after drying weighed 28.7 grams and had a melting range of 195° C. to 220° C. The third crop after drying weighed 2.7 grams and had a melting range of 197° C. to 200° C.

The first crop was analyzed for bromine. Calculated for $C_{10}H_5Br_4NO_3$: 63.07% Br. Found: 61.99%, 62.07% Br. Average Found: 62.03% Br. Infrared and nuclear magnetic resonance spectra of the first crop showed absorption bands expected for N-(2-hydroxyethyl)-tetrabromophthalimide. The purity according to the bromine analysis was 98.4 percent.

A sample of the first crop was subjected to thermogravimetric analysis in a flowing nitrogen atmosphere using a heating rate of 10° C. per minute. The results were a 1 percent weight loss at 225° C., a 5 percent weight loss at 298° C. and an 8 percent weight loss at 312° C.

EXAMPLE III

This example illustrates two syntheses of 2-(tetrabromophthalimido)ethyl chloroformate.

In the first synthesis, a 12 liter, 5-necked flask equipped with an agitator, a thermometer, an isopropanol and solid carbon dioxide cooled reflux condenser, a tube for the introduction of gaseous phosgene and an electric heating mantle was charged with 30.0 grams (0.38 mole) of pyridine and 6800 milliliters of chlorobenzene. Next was added 622.1 grams (6.28 moles) of phosgene at room temperature, as a gas, at the rate of 6.5 grams per minute. To the resulting solution was added, over a period of 1 hour, 1950.3 grams (3.85 moles) of solid N-(2-hydroxyethyl)tetrabromophthalimide. The reaction mixture was heated as the addition was made. At 70° C., a slight reflux of phosgene was observed. Upon completion of the addition, the reaction mixture was heated to 80° C. and held at that temperature for 1 hour. A drying tube was inserted in the top of the condenser and the reaction mixture was allowed to cool to room temperature overnight. On the next day, the reaction mixture was heated to 90° C. for 30 minutes, to 100° C. for 30 minutes, to 105° C. for 1 hour, to 110° C. for 2½ hours and to 115° C. for 30 minutes, whereupon a clear, brown solution was formed. The development of carbon dioxide was observed in the final stage of heating. A small aliquot of the reaction mixture was removed by a pipet and analyzed by liquid chromatography. The results are shown in Table 2.

TABLE 2

| Analytical Results | |
|---|---|
| Species Present | Analysis, Relative Percent By Weight |
| 2-(Tetrabromophthalimido)ethyl chloroformate | 52.0 |
| N—(2-Chloroethyl)-tetrabromophthalimide | 25.8 |
| N—(2-Hydroxyethyl)tetrabromophthalimide | 4.7 |
| Tetrabromophthalic anhydride | 5.6 |
| Chlorobenzene | 6.6 |

In the second synthesis, a 5 liter, 4-necked flask, equipped in the manner of the first synthesis, was charged with 2000 milliliters of chlorobenzene and 198.0 grams (2.0 moles) of gaseous phosgene. To the resulting solution was added over a period of 45 minutes 608.2 grams (1.2 moles) of solid N-(2-hydroxyethyl)-tetrabromophthalimide and 9.0 grams (0.114 mole) of pyridine. The reaction mixture was heated to 75° C. and the reflux of phosgene was observed. The temperature was raised gradually in 10° C. increments until a steady reflux of phosgene was observed. The reaction mixture was held at 115° C. for 2 hours and then allowed to cool to room temperature overnight. On the next day the reaction mixture was heated to 115° C. for 2 hours. A white sublimate of pyridine hydrochloride was observed in the cooler, upper parts of the flask. The isopropanol and solid carbon dioxide cooled condenser was replaced with a water cooled reflux condenser and the reaction mixture was slowly heated to reflux and maintained at reflux for 1 hour. At the end of this time the excess phosgene had been removed from the flask and absorbed by a scrubber containing aqueous sodium hydroxide. A small aliquot of the reaction mixture was removed using a pipet. Most of the chlorobenzene was removed from the aliquot in a round-bottomed flask on a flash evaporator, followed by filtration of the residue.

EXAMPLE IV

This example illustrates a synthesis of bis[2-(tetrabromophthalimido)ethyl]carbonate.

A one liter four-necked flask, equipped with an agitator, was charged with 60.0 grams (0.1184 mole) of N-(2-hydroxyethyl)-tetrabromophthalimide, 145.0 grams (1.83 mole) pyridine and 400 milliliters methylene chloride. To the charged materials was added 10.0 grams (0.101 mole) phosgene. A thick, white viscous mass was formed. The reaction mixture was stirred at room temperature for 2 hours and then poured into a four liter beaker. Two hundred fifty milliliters of 5% hydrochloric acid was added and a thick emulsion was observed to form. After standing at room temperature overnight, the emulsion was washed twice with 250 milliliter portions of 5% hydrochloric acid and twice with 250 milliliter portions of water. In each case the lower organic layer was separated from the upper aqueous layer in a separatory funnel and the aqueous layer was discarded. Upon the addition of 2000 milliliters of methanol to the organic layer, a fine white powder formed. The powder was removed by filtration and dried in vacuum oven at 120° C. for 8 hours. The dry weight yield was 54.9 grams or 89.2 percent of theory. The product was identified as bis-[2-(tetrabromophthalimido)ethyl]carbonate by infrared analysis. The product was analyzed for bromine. Calculated for $C_{21}H_8Br_8N_2O_7$: 61.49% Br. Found: 60.24%, 60.50% Br. Average Found: 60.40% Br. Based on the experimentally determined bromine content, the purity was 98.22 percent. According to the infrared spectrum, the purity was about 99 percent. The melting range was 263° C. to 265° C.

A sample of the product was subjected to thermogravimetric analysis using a 10° C./minute heating rate in a flowing nitrogen atmosphere. The results were a 1 percent weight loss at 217° C. and a 5 percent weight loss at 294° C.

EXAMPLE V

This example illustrates a synthesis of 2-(tetrabromophthalimido)ethyl pentabromophenyl carbonate.

A 500 milliliter four-necked flask equipped with an agitator, a thermometer, a reflux condenser and an electric heating mantle was charged with 25.0 grams of N-(2-hydroxyethyl)-tetrabromophthalimide, 26.4 grams of a mixture containing about 73% pentabromophenyl chloroformate and about 27% pentabromophenol, 300 milliliters p-xylene and 1.0 gram pyridine. The resulting off-white reaction mixture was stirred, heated to 100° C. and held at this temperature for 2 hours. The reaction mixture was heated to reflux and 3.3 grams pyridine was added through the condenser. After heating at reflux for 2 hours, the reaction mixture was cooled to 60° C. Seventy-five milliliters of 5 percent hydrochloric acid was added and the mixture was agitated to mix the materials. The reaction mixture was then allowed to stand quiescently to phase separate into an organic layer and an aqueous layer. The aqueous layer was removed with suction. The organic layer was washed with 75 milliliters of water and, after phase separation into an organic layer and an aqueous layer, the aqueous layer was removed with suction. The contents of the flask were poured into a 1 liter beaker containing 500 milliliters methanol. A fine white solid material was observed. The solids were removed by filtration and the filtrate was saved. The solids were washed with 500 milliliters of methanol, again removed by filtration and dried in a vacuum oven at 120° C. or 8 hours. The dry weight of this first crop of solids was 37.6 grams. The melting range was 220° C. to 230° C.

A second crop of solids was recovered by flash evaporation at reduced pressure from the saved filtrate and dried in a vacuum oven at 120° C. for 3 hours. The dry weight of the second crop of solids was 9.8 grams. The melting range was 155° C. to 165° C. The lower melting range and higher solubility in xylene and methanol of the second crop as compared to the first crop indicated that the second crop contained pentabromophenol.

A melting range of a 50/50 mixture of small amounts of the first and second crops was 175° C. to 190° C. The first crop was identified by infrared analysis to be about 65 to 70 weight percent 2-(tetrabromophthalimido)ethyl pentabromophenyl carbonate, about 30 to 35 weight percent N-(2-hydroxyethyl)-tetrabromophthalimide and less than about 5 weight percent pentabromophenol.

The first crop was analyzed for bromine. Calculated for $C_{17}H_4Br_9NO_5$: 70.41% Br. Found: 70.54%, 71.16% Br. Average Found: 70.85% Br. A sample of the first crop was subjected to thermogravimetric analysis using a 10° C./minute heating rate in a flowing nitrogen atmosphere. The results were a 1 percent weight loss at 217° C. and a 5 percent weight loss at 286° C.

A one liter four-necked flask equipped with an agitator, a water cooled condenser, a thermometer and an electric heating mantle was charged with 35.8 grams of the first crop of solids, 9.8 grams of the second crop of solids, 145.0 grams pyridine and 400 milliliters methylene chloride. The charged materials were stirred to form an off-white mixture containing some insoluble solids. Phosgene in the amount of 7.5 grams was added at the rate of 1.0 gram per minute. A brown liquid containing insoluble white solids formed. The contents of the flask were poured with stirring into a beaker containing 1500 milliliters of methanol. The solids were removed by filtration, washed with 250 milliliters distilled water, filtered, washed with 250 milliliters of methanol, filtered and dried in a vacuum oven at 120° C. for 2 hours to produce the principal product. The dry weight yield was 33.0 grams. The principal product was identified by infrared analysis to be 2-(tetrabromophthalimido)ethyl pentabromophenyl carbonate with a relative approximate abundance of 95 to 98 percent by weight. The melting range was 257° C. to 267° C. The results of bromine analysis were: calculated 70.41%; found, 70.89%, 70.60% by weight.

A sample of the principal product was subjected to thermogravimetric analysis using a 10° C./minute heating rate in a flowing nitrogen atmosphere. The results were a 1 percent weight loss at 246° C.±2° C. and a 5 percent weight loss at 312° C.±6° C.

EXAMPLE VI

This example illustrates a synthesis of pentabromophenyl chloroformate.

A 5 liter, four-necked flask equipped with an agitator, a thermometer, an isopropanol and solid carbon dioxide cooled reflux condenser, a tube for the introduction of gaseous phosgene and an electric heating mantle was charged with 2443.1 grams (5.0 moles) of pentabromophenol, 5.0 grams (0.07 mole) of imidazole and 7500 milliliters of diethyl carbonate. The charged materials were heated while gaseous phosgene was added at the rate of 8 grams per minute. The phosgene addition was begun while the temperature of the reaction mixture was at room temperature, and concluded when the temperature was 105° C. and 611.2 grams (6.17 moles) of phosgene had been added. The reaction mixture was then maintained at 90° C. for 1 hour, and thereafter allowed to cool overnight to room temperature. On the next day the reaction mixture was heated to 90° C. and maintained at temperatures in the range of from 90° C. to 96° C. for 8 hours while 171.3 grams (1.73 moles) of phosgene was added. The reaction mixture was then allowed to cool overnight to room temperature. On the following day the reaction mixture was briefly heated to 110° C. A clear, yellow solution was observed. A small aliquot was removed by a pipet and analyzed by liquid chromatography. The results showed that of the total dissolved solids in the solution, the relative percentages by weight of pentabromophenyl chloroformate and pentabromophenol were 87.7% and 1.8% respectively. The isopropanol and solid carbon dioxide cooled condenser was replaced with a water cooled condenser. Excess phosgene was purged by a stream of nitrogen which was bubbled through the reaction mixture for 8 hours while the reaction mixture was heated to the reflux temperature of diethyl carbonate. The nitrogen stream was terminated and 3000 milliliters of solvent was removed by distillation. Another small aliquot was removed and analyzed by liquid chromatography. The results showed that of the total dissolved solids in the solution, the relative percent by weight of pentabromophenyl chloroformate was 86.8% and the relative percent by weight of pentabromophenol was 1.6%.

The reaction mixture was allowed to cool to room temperature overnight whereupon a first crop of solids precipitated as a fine, white solid. The first crop was collected by filtration and dried in a vacuum oven for 3 hours at 70° C. and an absolute pressure of 0.5 Torr to yield 2033.0 grams of dry, white powder having a melting range of 80° C. to 102° C.

Differential scanning calorimetric analysis of the first crop at a heating rate of 10° C./minute in a flowing nitrogen atmosphere showed a melting point of 116° C. and decomposition at approximately 300° C. Gas chromatography showed the first crop to contain 0.08 percent by weight diethyl carbonate. The first crop was analyzed for bromine and chlorine. Calculated for $C_7Br_5ClO_2$: 72.50% Br, 6.43% Cl. Found: 70.10% Br, 69.90% Br, 6.25% Cl, 6.18% Cl. Average Found: 70.00% Br, 6.22% Cl. Purity was determined as follows: based on bromine content, 96.55%; based on chlorine content, 96.73%; based on liquid chromatography, 93.3 relative percent. According to liquid chromatography there was also present 3.1 relative weight percent bis(pentabromophenyl) carbonate. According to infrared spectroscopy, the first crop had the structure of pentabromophenyl chloroformate with no discernible impurities present; there was less than 0.02% hydroxyl present.

The filtrate from the first crop was concentrated in a flash evaporator to a volume of 1400 milliliters. This was filtered to recover a second crop of white solid. The second crop was dried in a vacuum oven for 8 hours at 70° C. and an absolute pressure of 0.5 Torr to yield 453.2 grams of an off-white solid. The pentabromophenyl chloroformate purity of the second crop was 88.5 percent by chloroformate titration and 86.6 relative percent by liquid chromatography.

EXAMPLE VII

This example illustrates a synthesis of 2-(tetrabromophthalimido)ethyl pentabromophenyl carbonate.

To a 12 liter, 4-necked flask equipped as in Example VI and containing 6350 milliliters of chlorobenzene, 661.3 grams (1.2 moles) of pentabromophenyl chloroformate and 2.4 grams (0.035 mole) of imidazole at 128° C. was added 608.2 grams (1.2 moles) of room temperature N-(2-hydroxyethyl)tetrabromophthalimide. The addition caused the temperature of the reaction mixture to drop to 90° C. The reaction mixture was heated to reflux (131° C.) and the evolution of gaseous hydrogen chloride was observed. The reflux was continued for 5 hours and then allowed to cool to room temperature, protected from atmospheric moisture by a drying tube atop the condenser. Approximately 2½ days later the reaction mixture was heated to 85° C. and 20.0 grams (0.202 mole) of phosgene was added. The reaction mixture was then heated at reflux (125° C.) for 1½ hours. Through the condenser was added 15.8 grams (0.2 mole) of pyridine. The reaction mixture was refluxed for 1 hour, then 8.0 grams (0.0808 mole) of phosgene was added with a slight reflux. Three and one-half liters of methanol was slowly added through the condenser; strong foaming and precipitation of the first crop of solids were observed. The first crop was collected by filtration and dried in a vacuum oven at 130° C. and an absolute pressure of 0.5 Torr for 4 hours to yield 562.6 grams of off-white solid. The melting range of the first crop was 260° C. to 270° C. Infrared spectroscopy confirmed the structure as that of 2-(tetrabromophthalimido)ethyl pentabromophenyl carbonate. The first crop was analyzed for bromine. Found 68.13%, 68.06% Br. Average Found: 68.10% Br. Calculated for $C_{17}H_4Br_9NO_5$: 70.14% Br. On the basis of bromine analysis, the purity of the first crop was 96.7 percent.

By gradual concentration of the filtrate from the first crop and by repeated filtration, second and third crops were obtained, which after drying in a manner similar to that of the first crop, weighed 437.3 grams and 127.7 grams, respectively. The second crop was an off-white solid, while the third crop was a yellowish solid.

A sample of the first crop was subjected to thermogravimetric analysis using a 10° C./minute heating rate in a flowing nitrogen atmosphere. The results were a 1 percent weight loss at 236° C., a 5 percent weight loss at 311° C. and an 8 percent weight loss at 324° C.

EXAMPLE VIII

This example illustrates a synthesis of 2-(tetrabromophthalimido)ethyl chloroformate and a synthesis of 2-(tetrabromophthalimido)ethyl pentabromophenyl carbonate.

A one liter, 4-necked flask equipped as in Example VI was charged with 200 milliliters of chlorobenzene, 0.45 gram (0.00569 mole) of pyridine and 8.3 grams (0.084 mole) of gaseous phosgene. To the resulting solution was added at room temperature 30.4 grams (0.06 mole) of N-(2-hydroxyethyl)tetrabromophthalimide. The resulting green slurry was heated to 75° C. for 1 hour, to 85° C. for 1 hour, to 110° C. for 1 hour, and then to 130° C., with reflux, for 1 hour. A clear, brown solution was obtained. The isopropanol and solid carbon dioxide cooled condenser was replaced by a water cooled condenser and the reaction mixture was heated at reflux for 1 hour with a nitrogen purge to produce a solution containing 2-(tetrabromophthalimido)ethyl chloroformate. While reflux conditions were maintained, 29.3 grams (0.06 mole) of pentabromophenol was added and the reaction mixture was refluxed for 3 hours. With the reaction mixture still at reflux, 8.5 grams (0.086 mole) of triphosgene was added. The reaction mixture was then held at reflux for 1 hour and then filtered to recover the first crop of product as a fine, white, crystalline solid.

The filtrate from the first crop was poured into 1.5 liters of methanol to precipitate the second crop which was collected by filtration as an off-white solid.

The first and second crops were both dried in a vacuum oven at 80° C. and an absolute pressure of 0.5 Torr to constant weights of 23.9 grams and 25.0 grams, respectively. The first crop had a melting range of 276° C. to 278° C. and melted to a clear, orange liquid. The second crop had a melting range of 225° C. to 235° C. and melted to a cloudy liquid which became a clear, yellow liquid at 270° C.

The first crop was identified as 2-(tetrabromophthalimido)ethyl pentabromophenyl carbonate by liquid chromatography and was analyzed for bromine and chlorine. Found: chlorine not detectable (less than 0.01% Cl). Average Found: 71.31% Br (average of five determinations). Based on bromine content the purity of the first crop was 98.74 percent. By liquid chromatography the relative purity was 88.6 percent and the sample also contained 6.5 relative percent of chlorobenzene.

The first crop was redried for 4 hours in a vacuum oven at 140° C. and an absolute pressure of 0.5 Torr. After redrying the relative purity was 95.4 percent and the sample contained 1.5 relative percent of chlorobenzene, as determined by liquid chromatography. The melting range was 276° C. to 278° C.

EXAMPLE IX

This example illustrates a synthesis of N-(2-hydroxyethyl)tribromophthalimide.

A 927.4 gram quantity of brominated phthalic anhydride containing from about 81.8% to about 97.0% tribromophthalic anhydride (position isomers undetermined) was distributed in equal amounts in two 4 liter beakers. To each beaker was added 2700 milliliters of chlorobenzene. The beakers were heated, with magnetic stirring, on two hot plates to 90° C. to 110° C., whereupon almost all of the solids dissolved.

In each of two 500 milliliter Erlenmeyer flasks, 61.1 grams of 2-aminoethanol was dissolved at 90° C. in 350 milliliters of chlorobenzene. At this temperature, with stirring, the contents of one flask were added to one beaker and the contents of the other flask were added to the other beaker. Each addition was completed in 15 minutes, and in these periods the temperature of the reaction mixtures in the beakers reached 110° C. The temperatures of the reaction mixtures were then maintained at 103° C. to 125° C. for 30 minutes while a precipitate was formed in each reaction mixture. The reaction mixtures were allowed to cool to 60° C. At this temperature the supernatant liquids were decanted from the precipitates and allowed to evaporate in a hood for 3 days to a small volume, whereupon more precipitates were formed. These precipitates were recovered by filtration and combined with the precipitates initially produced in the beakers to form a first crop. The first crop was washed with 800 milliliters of methanol, dried for 9 hours in a vacuum oven at 140° C. and an absolute pressure of 0.5 Torr, pulverized to a powder, dried in air for 24 hours at room temperature and dried for 5 hours in a vacuum oven at 160° C. to 165° C. and an absolute pressure of 0.5 Torr. The yield of the first crop was 917.3 grams of pale yellowish powder. Analysis by liquid chromatography indicated the sample contained 96.9 relative weight percent N-(2-hydroxyethyl)tribromophthalimide and 0.2 relative weight percent chlorobenzene.

The filtrate from the first crop was concentrated in a flash evaporator and filtered to recover a second crop of solids. The second crop was dried for 5 hours in a vacuum oven at 160° C. and an absolute pressure of 0.5 Torr and then ground to yield 156.1 grams of fine powder.

EXAMPLE X

This example illustrates a synthesis of 2-(tribromophthalimido)ethyl chloroformate.

A 5 liter, 4-necked flask equipped as in Example VI was charged with 2000 milliliters of chlorobenzene, 4.5 grams of pyridine and 105.7 grams of phosgene. Through a solids addition funnel was added over a period of 45 minutes 304.1 grams of the first crop product of Example IX. The resulting green slurry was heated at 75° C. for 1 hour, at 90° C. for 1 hour, at 100° C. for 1 hour and at 130° C. for 1 hour. Analysis of a small aliquot of the resulting clear, brown solutions by liquid chromatography indicated it contained 76.3 relative weight percent 2-(tribromophthalimido)ethyl chloroformate, 0.6 relative weight percent N-(2-chloroethyl)tribromophthalimide and 12.5 relative weight percent chlorobenzene. After withdrawal of the aliquot, the isopropanol and solid carbon dioxide cooled reflux condenser was replaced by a water cooled condenser. The reaction mixture was heated for 1 hour at 110° C. while a stream of nitrogen was bubbled through the solution. Analysis of a small aliquot by liquid chromatography showed the resulting product to contain 54.1 relative weight percent 2-(tribromophthalimido)ethyl chloroformate, 23.9 relative weight percent N-(2-chloroethyl)-tribromophthalimide and 10.9 relative weight percent chlorobenzene.

EXAMPLE XI

This example illustrates a synthesis of 2-(tribromophthalimido)ethyl pentabromophenyl carbonate.

To the product of Example X, which was still in the apparatus described in Example X, was added 293.2 grams of pentabromophenol. The reaction mixture was heated at reflux (131° C. to 132° C.) for 3½ hours. Initially, a clear, brown solution formed as pentabromophenol dissolved and soon thereafter a precipitate formed. After refluxing was completed, the reaction mixture was filtered while hot and the first crop of solids was collected. The first crop was dried in an air-oven at 85° C. for 88 hours and thereafter dried for 4 hours in a vacuum oven at 140° C. and an absolute pressure of 0.5 Torr to produce 314.0 grams of powder having a melting range of 277° C. to 280° C.

Liquid chromatographic analysis of the first crop indicated it was 100% 2-(tribromophthalimido)ethyl pentabromophenyl carbonate. The structure was confirmed by infrared spectroscopy. The first crop was also analyzed for bromine. Found: 67.78%, 67.79% Br. Average Found: 67.79% Br. Calculated for $C_{17}H_5Br_8NO_5$: 67.83% Br. On the basis of bromine analysis the purity of the first crop was 99.94 percent.

The filtrate from the first crop was evaporated to dryness to form a second crop of solids. Liquid chromatographic analysis showed the second crop to contain 7.8 relative weight percent 2-(tribromophthalimido)ethyl pentabromophenyl carbonate, 76.1 relative weight percent N-(2-chloroethyl)tribromophthalimide, 0.8 relative weight percent chlorobenzene and 2.3 relative weight percent pentabromophenol.

A sample of the first crop was subjected to thermogravimetric analysis in a flowing nitrogen atmosphere using a heating rate of 10° C. per minute. The results were a 1 percent weight loss at 269° C., a 5 percent weight loss at 310° C. and an 8 percent weight loss at 319° C. Differential scanning calorimetry in a nitrogen atmosphere at a heating rate of 10° C. per minute indicated the melting point of the first crop was 272° C. and showed decomposition to occur at about 300° C.

EXAMPLE XII

This example illustrates a synthesis of 2-(tetrabromophthalimido)ethyl 2,4,6-tribromophenyl carbonate.

To a 1 liter, 4-necked flask equipped as in Example VI was added 200 milliliters of chlorobenzene, 48.1 grams of gaseous phosgene and 0.75 gram of pyridine. Then, 50.7 grams of the second crop of Example I was added at room temperature through a solids addition funnel while stirring the reaction mixture. Thirty milliliters of chlorobenzene was next added through the solids addition funnel. The reaction mixture was heated in the range of from 90° C. to 100° C. for 30 minutes. The isopropanol and solid carbon dioxide cooled condenser was replaced with a water-cooled condenser and the reaction mixture was heated for about 1½ hours at 100° C. At the conclusion of this period the evolution of hydrogen chloride and excess phosgene had ceased. From the total volume of 280 milliliters of reaction mixture at 100° C., 28 milliliters was removed with a pipet. To the reaction mixture remaining in the flask at 100° C., was added 29.8 grams of 2,4,6-trimbromophenol as a white powder. A copious development of hydrogen chloride gas was observed. The reaction mixture was heated for 4 hours at 100° C. to 135° C. Twelve grams of gaseous phosgene was added at about 100° C. The reaction mixture was then allowed to cool to room temperature overnight, protected from atmospheric moisture by a drying tube above the condenser. On the next day the condenser was replaced with a water cooled condenser and the reaction mixture was heated to 130° C. and held at that temperature for 2 hours to remove the last of the hydrogen chloride and phosgene through the condenser. The reaction mixture was then cooled to 0° C. and mixed with one liter of hexane to precipitate a first crop of solids. The first crop was recovered by filtration, washed on the filter with 50 milliliters of heptane, dried in air for 30 minutes, dried in vacuum oven for 2½ hours at 120° C. and an absolute pressure of 0.5 Torr and dried in a vacuum oven for 2 hours at 130° C. and an absolute pressure of 0.5 Torr. The yield of the first crop was 57.0 grams. Of the first crop, 51.8 grams was dissolved in 300 milliliters of hot chlorobenzene. To the resulting solution was added 6.4 grams of decolorizing carbon. After removing the carbon by filtration, the filtrate was concentrated almost to dryness to form a white precipitate which was filtered. The white precipitate was washed on the filter with 200 milliliters of acetone and dried in a vacuum oven for 8 hours at 130° C. and an absolute pressure of 0.5 Torr to yield 24.4 grams of white solids. After pulverization to a white powder, 20.4 grams was dried in a vacuum oven for 4 hours at 160° C. and an absolute pressure of 0.5 Torr to yield 18.5 grams of principal product having a melting range of 221° C. to 224° C. The principal product was analyzed for bromine. Calculated for $C_{17}H_6Br_7NO_5$: 64.77% Br. Found: 64.99%, 64.92% Br. Average Found: 64.95% Br. On the basis of bromine analysis the purity of the principal product was 99.71 percent. Analysis by liquid chromatography showed the principal product to contain 85.4 relative weight percent 2-(tetrabromophthalimido)ethyl 2,4,6-tribromophenyl carbonate. A sample of the principal product was subjected to thermogravimetric analysis using a 10° C./minute heating rate in a flowing nitrogen atmosphere. The results were a 1 percent weight loss at about 235° C., a 5 percent weight loss at 322° C. and an 8 percent weight loss at 334° C.

The filtrate from the white precipitate was combined with the acetone washings, evaporated to near dryness in a flash evaporator, filtered and dried to yield 14.0 grams of white solid as a second crop. Analysis by liquid chromatography showed this to contain 33.7 relative weight percent 2-(tetrabromophthalimido)ethyl 2,4,6-tribromophenyl carbonate, the presence of which is confirmed by infrared spectroscopy.

Solvent was removed from the filtrate from the first crop on a flash evaporator to form a precipitate. The almost dry precipitate was transferred to a filter with about 50 milliliters of heptane and about 10 milliliters of acetone. After filtration and drying, the yield of the resulting third crop was 18.3 grams. Analysis by liquid chromatography showed the third crop to contain 21.5 relative weight percent 2-(tetrabromophthalimido)ethyl 2,4,6-tribromophenyl carbonate.

EXAMPLE XIII

This example illustrates a synthesis of N-(5-hydroxypentyl)tetrachlorophthalimide.

A 4 liter beaker was charged with 128.7 grams (0.45 mole) of tetrachlorophthalic anhydride and 800 milliliters of toluene. The charged materials were heated to form a solution. To this solution at 104° C. was added in 18 minutes with magnetic stirring, a solution of 46.4 grams (0.45 mole) of 5-amino-1-pentanol dissolved in 400 milliliters of toluene. The resulting clear, pale yellowish solution was heated in the beaker covered by a watch glass at 106° C. for 1 hour. The solution was then concentrated on a flash evaporator to a volume of 800 milliliters and cooled to room temperature. The white solid which formed was collected by filtration, washed with 200 milliliters of toluene at room temperature, dried for 16 hours in the air, dried for 30 minutes at 100° C. in a hot air oven, dried for 4 hours in a vacuum oven at 90° C. and an absolute pressure of 0.5 Torr, pulverized, and dried for 2 hours in a vacuum oven at 120° C. and an absolute pressure of 0.5 Torr to yield 117.2 grams of a first crop of solids.

The joined toluene filtrate and washings from the first crop were concentrated on a flash evaporator to near dryness. The resulting solids were transferred to a filter with about 20 milliliters of methanol and washed with 50 milliliters of hexane. The solids were air dried for 2 hours, dried in a vacuum oven for 3 hours at 90° C. and an absolute pressure of 0.5 Torr and dried for 8 hours in a vacuum oven at 130° C. and an absolute pressure of 0.5 Torr to yield 43.6 grams of a second crop of solids having a melting range of 150° C. to 152° C.

The first crop was analyzed for chlorine. Calculated for $C_{13}H_{11}Cl_4 NO_3$: 38.22%. Found: 37.51%, 37.96% Cl. Average Found: 37.74% Cl. The purity based on chlorine analysis was 98.74 percent. Infrared spectral analysis showed the first crop as containing 4.46% OH; purity based on this figure was 97.38 percent. Analysis by liquid chromatography showed the first crop to contain 96.2 relative weight percent N-(5-hydroxypentyl)tetrachlorophthalimide and 0.6 relative weight percent toluene. The structure was confirmed by infrared and nuclear magnetic resonance spectra which indicated a purity of 95 to 99 percent.

Analysis of the second crop by liquid chromatography showed it to contain 97.5 relative weight percent N-(5-hydroxypentyl)-tetrachlorophthalimide and 0.7 relative weight percent toluene.

EXAMPLE XIV

This example illustrates a synthesis of 2,4-dibromo-3,5,6-trichlorophenol.

A 1 liter, 4-necked flask equipped with an agitator, a thermometer, a water cooled reflux condenser, a dropping funnel and an electric heating mantle was charged with 500 milliliters of glacial acetic acid and 49.5 grams (0.2507 mole) of 2,3,5-trichlorophenol. To the charged materials was added 0.5 gram (0.00375 mole) of aluminum chloride, which dissolved. From the dropping funnel was added over a period of 15 minutes, 96.0 grams (0.6 mole) of liquid bromine, whereupon the temperature increased spontaneously from 26° C. to 39° C. The reaction mixture was refluxed at 110° C. for 5 hours and then allowed to cool to room temperature overnight. The resulting reaction mixture was a pale orange liquid with some white solids present.

The reaction mixture was filtered at room temperature. The resulting first crop of solids was washed with 100 milliliters of acetic acid, dried for 3 hours in an air oven at 100° C. and dried for 4 hours in a vacuum oven at 140° C. and an absolute pressure of 0.5 Torr to yield 23.6 grams of dried solids having a melting range of 187° C. to 189° C.

The filtrate from the first crop was admixed with 2 liters of ice water to precipitate the second crop of solids. The mixture was filtered to remove the second crop, which was washed with 100 milliliters of distilled water and dried in the manner of the first crop. The yield of dried solids was 55.4 grams. The melting range was 172° C. to 183° C.

A solution was prepared by dissolving 55.2 grams of the second crop in 500 milliliters of diethyl ether. The solution was filtered through 6.4 grams of decolorizing carbon powder and concentrated on a flash evaporator to a volume of 200 milliliters. One hundred milliliters of heptane was added and the composition was concentrated on the flash evaporator to a volume of 100 milliliters to precipitate the third crop of solids. The third crop was separated by filtration, washed with 140 milliliters of heptane and dried in the manner of the first crop. The yield of dried solids was 37.4 grams. The melting range was 185° C. to 186° C.

A fourth crop of solids was obtained by evaporating to substantial dryness the heptane filtrate and washings from the third crop and drying in the manner of the first crop. The yield of dried solids was 12.8 grams. Each of the four crops was analyzed by liquid chromatography; the results are shown in Table 3.

TABLE 3

| Crop | Analytical Results Purity, Relative Weight Percent 2,4-dibromo-3,5,6-trichlorophenol |
|---|---|
| 1 | 96.3 |
| 2 | 90.4 |
| 3 | 97.1 |
| 4 | 80.4 |

The structure of 2,4-dibromo-3,5,6-trichlorophenol was confirmed in the first crop by infrared and nuclear magnetic resonance spectroscopy. The infrared spectrum of the third crop was identical to that of the first crop. Liquid chromatography also showed that the fourth crop contained 11.6 relative weight percent 4-bromo-2,3,5-trichlorophenol and 5.6 relative weight percent 6-bromo-2,3,5-trichlorophenol.

The first crop was analyzed for bromine and chlorine. Calculated for $C_6HBr_2Cl_3O$: 44.99% Br, 29.94% Cl. Found: 44.73%, 45.17% Br; 29.17%, 28.03% Cl. Average Found: 44.95% Br; 28.60% Cl.

EXAMPLE XV

This example illustrates a synthesis of 5-(tetrachlorophthalimido)pentyl chloroformate.

A 2 liter, 4-necked flask equipped as in Example VI was charged with 800 milliliters of chlorobenzene and 1.0 gram of pyridine. To the resulting solution at 30° C. was added over a period of 12 minutes, 53.1 grams of gaseous phosgene. Then, over a period of 40 minutes, 72.2 grams of the first crop of Example XIII was added through a solids addition funnel. The temperature of the reaction mixture during this addition was from 35° C. to 70° C. One hundred milliliters of chlorobenzene was added through the solids addition funnel. The reaction mixture was heated for 1 hour at 75° C., for 1 hour at 85° C. and for 1 hour at 105° C. The isopropanol and solid carbon dioxide cooled condenser was replaced with a water cooled condenser. A stream of nitrogen was introduced to remove hydrogen chloride and phosgene. The product was pale orange solution containing about 1 gram of pyridine hydrochloride precipitate.

A 180 milliliter sample of the solution was removed from the flask. One hundred seventy-eight milliliters of the sample was concentrated to substantial dryness on a flash evaporator. The solid residue was transferred to a filter with 30 milliliters of hexane, separated from the liquid by filtration, dried for 16 hours in a vacuum oven at 50° C. and an absolute pressure of 0.5 Torr and dried in a vacuum oven for 4 hours at 25° C. and an absolute pressure of 0.5 Torr to yield 13.0 grams of white solid having a melting range of 108° C. to 110° C. Liquid chromatographic analysis showed the white solid to contain 63.2 relative weight percent 5-(tetrachlorophthalimido)pentyl chloroformate, 29.4 relative weight percent N-(5-chloropentyl)-tetrachloropthalimide, 6.1 relative weight percent N-(5-hydroxypentyl)-tetrachlorophthalimide and 1.3 relative weight percent chlorobenzene. By titration of the reactive chloroformate chlorine, the purity was found to be 65.42%, 66.08%, average: 65.75%. Structures of the two major components were confirmed by infrared and nuclear magnetic resonance spectra. The infrared spectrum also showed a hydroxyl content of 0.73 percent, which corresponds to 15.93 percent N-(5-hydroxypentyl)-tetrachlorophthalimide in the sample. The sample was analyzed for chlorine. Calculated for $C_{14}H_{10}Cl_5NO_4$: 40.89% Cl. Found: 40.08%, 39.97% Cl. Average Found: 40.02% Cl.

EXAMPLE XVI

This example illustrates a synthesis of 5-(tetrachlorophthalimido)pentyl 2,4-dibromo-3,5,6-trichlorophenyl carbonate.

The the product of Example XV which had not been removed from the flask was added through a solids addition funnel 55.3 grams of 2,4-dibromo-3,5,6-trichlorophenol taken from the first and third crops of Example XIV. Immediately thereafter, 330 milliliters of chlorobenzene was added at room temperature. The reaction mixture was heated for 4 hours at 130° C. with the elimination of gaseous hydrogen chloride which escaped through the water cooled condenser.

The reaction mixture was cooled to room temperature to precipitate a first crop of solids. The reaction mixture was filtered to remove the first crop which was then dried for 16 hours at room temperature and then dried for 16 hours in a vacuum oven at 70° C. and an absolute pressure of 0.5 Torr to yield 5.1 grams of solid having a melting range of 93° C. to 103° C.

The filtrate from the first crop was concentrated by distillation of chlorobenzene to a volume of about 100 milliliters and then cooled to room temperature to precipitate a second crop of solids. The second crop was separated by filtration, washed successively with 50 milliliters of chlorobenzene and 100 milliliters of methanol and dried in the manner of the first crop to yield 63.0 grams of solid. After further drying for 4 hours in a vacuum oven at 110° C. and an absolute pressure of 0.5 Torr, the melting range of the second crop was 127° C. to 130° C.

The filtrate and chlorobenzene washings from the second crop were distilled to dryness to form a third crop of solids. The third crop was transferred to a filter with 10 milliliters of methanol and filtered. The third crop was then dried in the manner of the first crop to yield 4.9 grams of solid having a melting range of 112° C. to 119° C.

A fourth crop was formed by distilling to dryness the methanol washings from the third crop and drying in the manner of the first crop. The yield was 7.1 grams of solid having a melting range of 86° C. to 94° C.

Each of the four crops was analyzed by liquid chromatography; the results are shown in Table 4.

TABLE 4

| | Analytical Results Relative Weight Percent | | |
|---|---|---|---|
| Crop | A | B | C |
| 1 | 39.6 | 58.8 | 1.7 |
| 2 | 76.7 | 15.4 | 0.8 |
| 3 | 79.7 | 18.2 | 2.1 |
| 4 | 57.8 | 31.6 | 1.3 |

A = 5-(tetrachlorophthalimido)pentyl 2,4-dibromo-3,5,6-trichlorophenyl carbonate.
B = N—(5-chloropentyl)-tetrachlorophthalimide.
C = chlorobenzene The second crop was analyzed for bromine and chlorine. Calculated for $C_{20}H_{10}Br_2Cl_7NO_5$: 21.24% Br, 32.99% Cl. Found: 19.11%, 19.35% Br; 33.08%, 33.10% Cl. Average Found: 19.23% Br, 33.09% Cl.

By differential scanning calorimetry in a flowing nitrogen atmosphere at a heating rate of 10° C./minute, the melting point of the second crop was 105° C. and decomposition occurred at about 300° C. Thermogravimetric analysis in a flowing nitrogen atmosphere at a heating rate of 10° C./minute indicated for the second crop a 1 percent weight loss at 185°, a 5 percent weight loss at 284° C. and an 8 percent weight loss at 304° C.

EXAMPLE XVII

This example illustrates a synthesis of bis[5-(tetrachlorophthalimido)pentyl] carbonate.

A 2 liter, 4-necked flask equipped as in Example VI was charged with 77.8 grams of N-(5-hydroxypentyl)-tetrachlorophthalimide taken from the first and second crops of Example XIII, one liter of toluene, 21.3 grams of triethylamine and 1.7 grams of pyridine. The charged materials were heated to 57° C. to dissolve the solids. The resulting solution was cooled to 30° C. by an external ice water bath and at this temperature the addition of phosgene at a rate of 1 gram per minute was begun. After 16 minutes the addition was completed. The reaction mixture was heated for 1 hour at 80° C. and then the hot reaction mixture was poured into 2 liters of methanol to form a first crop of solids. The first crop was recovered by filtration, washed with 150 milliliters of methanol, pulverized and dried for 4 hours in a vacuum oven at 120° C. to yield 46.6 grams of solid having a melting range of 214° C. to 217° C.

Liquid chromatographic analysis using a mixture of 18 percent dioxane and 82 percent hexane for elution showed the first crop to contain 83.8 relative weight percent bis[5-(tetrachlorophthalimido)pentyl] carbonate and 9.5 relative weight percent 5-(tetrachlorophthalimido)pentyl chloroformate.

Liquid chromatographic analysis using a mixture of 5 percent dioxane and 95 percent hexane for elution showed the first crop to contain 88.2 relative weight percent bis[5-(tetrachlorophthalimido)pentyl] carbonate, 9.8 relative weight percent 5-(tetrachlorophthalimido)pentyl chloroformate and 0.7 relative weight percent N-(5-chloropentyl)-tetrachlorophthalimide.

The first crop was also analyzed for chlorine. Calculated for $C_{27}H_{20}Cl_8N_2O_7$: 36.92% Cl. Found: 35.86% Cl. Average Found: 35.86% Cl.

Thermogravimetric analysis of the first crop in a flowing nitrogen atmosphere using a heating rate of 10° C./minute indicated a 1 percent weight loss at 196° C., a 5 percent weight loss at 287° C. and an 8 percent weight loss at 312° C.

The methanol and toluene filtrate from the first crop was admixed with the methanol washings. The mixture was evaporated to near dryness on a flash evaporator. The resulting second crop of solids was transferred to a filter with 200 milliliters of hexane. The second crop was recovered by filtration and dried for 4 hours in a vacuum oven at 65° C. to yield 59.7 grams of solid. The second crop was found by infrared spectroscopy to contain bis[5-(tetrachlorophthalimido)pentyl] carbonate together with some other materials, including triethylamine hydrochloride and pyridine hydrochloride.

EXAMPLE XVIII

A series of compositions, each containing an additive to be evaluated, antimony trioxide and acrylonitrile-butadiene-styrene interpolymer, were tested for fire retardance. For each of the compositions tested, acrylonitrile-butadiene-styrene interpolymer (ABS) was introduced into a mixer and melted. A mixture of the additive to be evaluated and antimony trioxide was added to the melt and the materials were mixed until uniform to produce the composition. After cooling, each composition was chopped into small pieces and extruded into one-eighth inch pellets. The pellets were injection molded into bars. The identities of the additives and the proportions of materials in the bars and the results are shown in Table 6.

TABLE 6

TESTING OF COMPOSITIONS FOR FIRE RETARDANCE

| | | Proportions, Parts by Weight | | | Vertical Burning Test UL 94 | | ASTM Method D 2863-70 | | |
|---|---|---|---|---|---|---|---|---|---|
| Run | Additive | HIPS | Additive | Antimony Trioxide | Classification | After Flame Time, seconds | Oxygen Index, percent $O_2$ by volume | Charring | Melting |
| 1 | Principal Product of Example V | 100 | 12 | 4 | 94V-0 | 1.5 | 24.0 | Yes | No |
| 2 | First Crop of Example VII | 100 | 12 | 4 | 94V-0 | 4.4 | 25.5 | Yes | No |
| 3 | Redried First Crop of Example VIII | 100 | 12 | 4 | 94V-0 | 1.8 | 25.0 | Yes | No |
|   |   | 100 | 12 | 4 | 94V-0 | 1.5 | 24.0 | Yes | No |
| 4 | Product of Example IV | 100 | 12 | 4 | 94V-2 | 10.6 | 23.0 | No | Yes |
| 5 | (See Note 2) | 100 | 12 | 4 | 94V-2 | 10.9 | 24.5 | Yes | No |
| 6 | First Crop of Example XI | 100 | 12 | 4 | Fails | >30 | 24.5 | Not Recorded | Not Recorded |

Note 2:
The additive of Run 5 was the same as the additive of Run 3 of Example XVIII. See Note 1 of Table 5.

injection molded into bars. The identities of the additives and the proportions of materials in the bars are shown in Table 5. The bars were tested for flammability in accordance with the procedure of Vertical Burning Test UL 94, dated Feb. 1, 1974, of Underwriters Laboratories, Inc., and in accordance with ASTM Standard Method D 2863-70. The results are shown in Table 5.

EXAMPLE XX

Two series of compositions and bars of the compositions were prepared using the general procedure of Example XVIII. HIPS was employed rather than ABS, and the additive in each case was the first crop of Example VII. In the first series, the compositions contained

TABLE 5

TESTING OF COMPOSITIONS FOR FIRE RETARDANCE

| | | Proportions, Parts by Weight | | | Vertical Burning Test UL 94 | | ASTM Method D 2863-70 | | |
|---|---|---|---|---|---|---|---|---|---|
| Run | Additive | ABS | Additive | Antimony Trioxide | Classification | After Flame Time, seconds | Oxygen Index, percent $O_2$ by volume | Charring | Melting |
| 1 | Principal Product of Example V | 100 | 15 | 5 | 94V-2 | 1 | 28.0 | Yes | No |
| 2 | First Crop of Example VII | 100 | 15 | 5 | 94V-2 | 7.2 | 24.5 | Yes | No |
| 3 | (See Note 1) | 100 | 15 | 5 | 94V-2 | 9.9 | 27.0 | Yes | No |
| 4 | Second Crop of Example XVI | 100 | 61.2 | 10.3 | 94V-0 | 0.0 | 36.5 | Yes | No |
| 5 | Principal Product of Example XII | 100 | 15 | 5 | 94V-2 | 6.5 | 26.0 | Yes | No |
|   |   |   | 20.8 | 4.5 | 94V-2 | 6.5 | 27.5 | Yes | No |
| 6 | Product of Example IV | 100 | 15 | 5 | Fails | >30 | 27.5 | Yes | No |
|   |   |   |   |   |   |   | 26.5 | Yes | No |

Note:
The additive of Run 3 was prepared by the general methods of Examples VI and VII. The yield of the additive was 74.7% based on pentabromophenyl chloroformate; it was a fine, white solid. The structure for 2-(tetrabromophthalimido)ethyl pentabromophenyl carbonate was confirmed by infrared spectroscopy. The results of bromine analysis were Found: 69.39% Br; 69.72% Br; Average Found: 69.56% Br.

EXAMPLE XIX

A series of compositions and bars of the compositions were prepared using the general procedure of Example XVIII. High impact polystyrene (HIPS) was employed rather than ABS. The bars were tested for flammability as in Example XVIII. The identities of additives, the proportions of materials in the bars and the results are shown in Table 6.

16 parts of additive and antimony trioxide, taken together, per 100 parts of HIPS. In the second series, the compositions contained 18 parts of additive and antimony trioxide, taken together, per 100 parts of HIPS. The bars were tested for flammability as in Example XVIII. A blank containing no additive or antimony trioxide was also tested for Vertical Burning Test UL 94 Classification. The proportions of materials in the bars and the results are shown in Table 7.

TABLE 7

| | Proportions, Parts by Weight | | | Vertial Burning Test UL 94 | | ASTM Method D 2863-70 |
|---|---|---|---|---|---|---|
| Run | HIPS | Additive | Antimony Trioxide | Classification | After Flame Time, seconds | Oxygen Index, percent $O_2$ by volume |
| 1 | 100 | 12.000 | 4.000 | 94V-2 | 5.0 | 25.0 |
| 2 | 100 | 12.800 | 3.200 | 94V-2 | 7.8 | 25.0 |
| 3 | 100 | 13.333 | 2.667 | 94V-1 | 4.7 | 24.5 |
| 4 | 100 | 13.714 | 2.286 | Fails | >30 | 24.5 |
| 5 | 100 | 9.000 | 9.000 | 94V-1 | 13.3 | 25.5 |
| 6 | 100 | 12.000 | 6.000 | 94V-1 | 2.8 | 24.0 |
| 7 | 100 | 13.500 | 4.500 | 94V-0 | 0.7 | 25.5 |
| 8 | 100 | 14.400 | 3.600 | 94V-0 | 0.6 | 25.5 |

TABLE 7-continued

| Run | HIPS | Proportions, Parts by Weight Additive | Antimony Trioxide | Vertial Burning Test UL 94 Classification | After Flame Time, seconds | ASTM Method D 2863-70 Oxygen Index, percent O$_2$ by volume |
|---|---|---|---|---|---|---|
| 9 | 100 | 15.000 | 3.000 | 94V-0 | 0.7 | 26.0 |
| 10 | 100 | 15.429 | 2.571 | 94V-0 | 1.2 | 26.5 |
| 11 | 100 | 0 | 0 | Fails | >30 | Not Tested |

The compositions of Runs 8 and 11 were tested for physical properties. The results are shown in Table 8.

TABLE 8
TESTING OF COMPOSITIONS FOR PHYSICAL PROPERTIES

| TEST | Composition Run 8 | Run 11 |
|---|---|---|
| Tensile Strength, pounds/square inch | 3850 | 3975 |
| Tensile Modulus, pounds/square inch | 5625 | 4450 |
| Flexural Strength, pounds/square inch | 8100 | 7750 |
| Izod Impact Strength, foot-pounds | 0.57 | 1.92 |
| Heat Distortion Temperature, °C. | 79 | 74 |
| Melt Index, grams/10 minutes | 6.0 | 3.5 |

EXAMPLE XXI

A series of compositions and bars of the compositions were prepared using the general procedure of Example XVIII. High density polyethylene (HDPE) was employed rather than ABS. The bars were tested for flammability as in Example XVIII. The identities of additives, the proportions of materials in the bars and the results are shown in Table 9.

TABLE 9
TESTING OF COMPOSITIONS FOR FIRE RETARDANCE

| Run | Additive | Proportions, Parts by Weight HDPE | Additive | Antimony Trioxide | Vertical Burning Test UL 94 Classification | After Flame Time, seconds | ASTM Method D 2863-70 Oxygen Index, percent O$_2$ by volume | Charring | Melting |
|---|---|---|---|---|---|---|---|---|---|
| 1 | Principal Product of Example V | 100 | 10 | 5 | 94V-2 | 10.3 | 23.0 | No | Yes |
| 2 | (See Note 3) | 100 | 10 | 5 | 94V-2 | 2.2 | 25.0 | No | Yes |
| 3 | Redried First Crop of Example VIII | 100 | 10 | 5 | 94V-2 | 0.3 | 29.0 | No | Yes |
| | | 100 | 10 | 5 | 94V-2 | 10.3 | 23.0 | No | Yes |
| 4 | First Crop of Example XI | 100 | 10 | 5 | 94V-2 | 0.3 | 29.0 | Not Recorded | Yes |
| 5 | Principal Product of Example XII | 100 | 10 | 5 | 94V-0 | 0.0 | 28.0 | No | No |
| 6 | Product of Example IV | 100 | 10 | 5 | Fails | >30 | 23.0 | No | Yes |

Note 3:
The additive of Run 2 was the same as the additive of Run 3 of Example XVIII. See Note 1 of Table 5.

Although the present invention has been described with reference to specific details of certain embodiments thereof, it is not intended that such details should be regarded as limitations upon the scope of the invention except insofar as they are included in the accompanying claims.

I claim:

1. A compound represented by the structural formula:

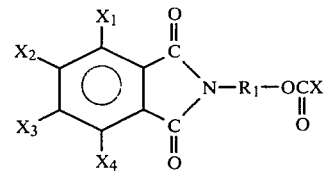

wherein:
a. $R_1$ is straight chain or branched chain alkylene having from about 2 to about 5 carbon atoms,
b. X is chloro or bromo, and
c. $X_1$, $X_2$, $X_3$, and $X_4$ are each independently hydrogen, chloro or bromo, with the proviso that at least three of $X_1$, $X_2$, $X_3$, and $X_4$ are each independently chloro or bromo.

2. The compound of claim 1 wherein $R_1$ is ethylene.

3. The compound of claim 1 wherein $X_1$, $X_2$, $X_3$, and $X_4$ are each independently chloro or bromo.

4. The compound of claim 1 wherein $X_1$, $X_2$, $X_3$ and $X_4$ are each bromo.

5. The compound of claim 4 wherein $R_1$ is ethylene.

* * * * *